United States Patent
Radwanski et al.

(10) Patent No.: US 6,734,157 B2
(45) Date of Patent: May 11, 2004

(54) CONTROLLED RELEASE ANTI-MICROBIAL HARD SURFACE WIPER

(75) Inventors: Fred R. Radwanski, Stone Mountain, GA (US); James W. Clark, Roswell, GA (US); Ralph L. Anderson, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/746,720

(22) Filed: Dec. 22, 2000

(65) Prior Publication Data

US 2002/0006887 A1 Jan. 17, 2002

Related U.S. Application Data

(60) Provisional application No. 60/173,224, filed on Dec. 28, 1999.

(51) Int. Cl.$^7$ .......................... C11D 17/04; B32B 05/16
(52) U.S. Cl. .................. 510/439; 510/109; 510/380; 510/382; 510/391; 428/323; 442/285
(58) Field of Search ................. 510/439, 380, 510/382, 391, 109; 428/323; 442/285

(56) References Cited

U.S. PATENT DOCUMENTS

| | | | |
|---|---|---|---|
| 2,449,274 A | 9/1948 | Broll | 167/33 |
| 2,542,909 A | 2/1951 | De Wet | 167/84 |
| 2,702,780 A | 2/1955 | Lerner | 167/84 |
| 3,060,079 A | 10/1962 | Pattilloch | 162/161 |
| 3,400,420 A | 9/1968 | Granville et al. | 15/104.93 |
| 3,640,841 A | 2/1972 | Winslow et al. | 162/164 |
| 3,663,262 A | 5/1972 | Cogan, Jr. | 117/62.1 |
| 3,704,096 A | 11/1972 | Verses et al. | 23/230 R |
| 3,857,934 A | 12/1974 | Bernstein et al. | 424/30 |
| 3,983,209 A | 9/1976 | Schmitt | 424/78 |
| 4,045,364 A | 8/1977 | Richter | 252/106 |
| 4,064,213 A | 12/1977 | Lazorisak et al. | 264/134 |
| 4,102,998 A | 7/1978 | Gutnick | 424/115 |
| 4,125,659 A | 11/1978 | Klowak et al. | 428/153 |
| 4,188,447 A | 2/1980 | Ehlenz | 428/310 |
| 4,205,043 A | 5/1980 | Esch et al. | 422/56 |
| 4,248,597 A | 2/1981 | McNeely | 23/230 R |
| 4,311,479 A * | 1/1982 | Fenn et al. | 8/495 |
| 4,323,557 A | 4/1982 | Rosso et al. | 424/28 |
| 4,343,788 A | 8/1982 | Mustacich et al. | 424/78 |
| 4,404,196 A | 9/1983 | Daudt et al. | 424/184 |
| 4,424,060 A | 1/1984 | Nakamura et al. | 8/115.5 |
| 4,436,780 A | 3/1984 | Hotchkiss et al. | 428/198 |
| 4,443,222 A | 4/1984 | Morris et al. | 8/189 |
| 4,454,110 A | 6/1984 | Caslavsky et al. | 424/54 |
| 4,496,322 A | 1/1985 | Sandham et al. | 433/217 |
| 4,504,442 A | 3/1985 | Rosenblatt et al. | 422/37 |
| 4,515,703 A | 5/1985 | Haq | 252/92 |
| 4,533,435 A | 8/1985 | Intili | 162/161 |
| 4,547,381 A | 10/1985 | Mason et al. | 426/316 |
| 4,563,184 A | 1/1986 | Korol | 604/368 |
| 4,563,351 A | 1/1986 | Caslavsky et al. | 424/151 |

(List continued on next page.)

FOREIGN PATENT DOCUMENTS

| | | | |
|---|---|---|---|
| DE | 2625176 B2 | 12/1977 | C11D/17/04 |
| DE | 2838523 A1 | 3/1980 | A47K/3/00 |
| EP | 0080382 A2 | 6/1983 | D04H/1/56 |
| EP | 0113254 A1 | 7/1984 | D04H/1/58 |
| EP | 0351907 A2 | 1/1990 | A01N/25/34 |
| EP | 0259113 B1 | 10/1990 | A61K/9/22 |
| EP | 0407943 A1 | 1/1991 | A61F/13/00 |
| EP | 0280571 B1 | 4/1993 | A61K/9/22 |
| EP | 0285209 B1 | 5/1993 | A01N/37/34 |
| EP | 0351580 B1 | 5/1993 | A61K/9/22 |
| EP | 0290676 B1 | 8/1994 | C09D/133/00 |
| EP | 0265906 B1 | 4/1995 | A61F/13/00 |
| EP | 0677296 A2 | 10/1995 | A61L/2/20 |
| EP | 0518445 B1 | 4/1996 | A23L/3/3571 |
| EP | 0709507 A1 | 5/1996 | D04H/1/64 |
| EP | 0552151 B1 | 3/1997 | A61K/31/74 |
| EP | 0761243 A1 | 3/1997 | A61L/29/00 |
| EP | 0537774 B1 | 1/1998 | A61K/6/083 |
| EP | 0838224 A2 | 4/1998 | A61K/47/48 |
| EP | 0852148 A1 | 7/1998 | A61L/15/46 |
| EP | 0858810 A2 | 8/1998 | A61L/25/00 |
| EP | 0861659 A1 | 9/1998 | A61K/9/32 |
| EP | 0866103 A1 | 9/1998 | C09D/5/14 |

(List continued on next page.)

OTHER PUBLICATIONS

"Method 8167 Powder Pillows or AccuVac® Ampuls," adapted from *Standard Mehtods for the Examination of Water and Wastewater*, 12/01, 3ed. by Hach Company, U.S.A.

"Hycar Reactive Liquid Polymers—The Key to Building Superior Products," 1998, Noveon, Inc., U.S.A.

Wilkinson, Sophie L., "Eating Safely in a Dirty World," C&EN, Nov. 10, 1997, pp. 24–28 & 33.

Material Safety Data Sheet published by Sybron Chemicals, Inc. of Birmingham, NJ regarding XAMA®–7 IONAC® Polyfunctional Axiridine (no date available).

Hy–Lite™ Data Logger Operator's Manual included with machiens published by EM Science, a Division of EM Industries, Inc. (no date available).

Information Sheet entitled "Hygiene Monitoring in Place" Hy–Lite™ published by EM Science, a Division of EM Industries, Inc. (no date available).

(List continued on next page.)

*Primary Examiner*—Lorna M. Douyon
(74) *Attorney, Agent, or Firm*—Nelson Mullins Riley & Scarborough

(57) ABSTRACT

A wiper that provides a controlled release anti-microbial agent has a substrate layer to which the anti-microbial agent is adhered. In addition, the wiper will have one or more laminate layers, at least one of which will be absorbent. Various anti-microbial agents such as silver containing additives, calcium hypochlorite, and chlorine dioxide generating compounds may be employed. The substrate layer may be a poly(ethylene vinyl acetate) meltblown web and the laminate layer may be a hydroentangled composite absorbent fabric.

54 Claims, No Drawings

U.S. PATENT DOCUMENTS

| | | | |
|---|---|---|---|
| 4,568,535 A | 2/1986 | Loesche | 424/19 |
| 4,568,536 A | 2/1986 | Kronenthal et al. | 424/22 |
| 4,600,620 A * | 7/1986 | Lloyd et al. | 428/195 |
| 4,615,697 A | 10/1986 | Robinson | 604/890 |
| 4,615,705 A | 10/1986 | Scales et al. | 623/11 |
| 4,615,937 A | 10/1986 | Bouchette | 428/288 |
| 4,659,609 A | 4/1987 | Lamers et al. | 428/194 |
| 4,661,344 A | 4/1987 | Relenyi | 424/79 |
| 4,668,228 A | 5/1987 | Bolton et al. | 604/307 |
| 4,675,347 A | 6/1987 | Mochizuki et al. | 523/122 |
| 4,678,704 A | 7/1987 | Fellows | 428/289 |
| 4,681,739 A | 7/1987 | Rosenblatt et al. | 422/37 |
| 4,689,169 A | 8/1987 | Mason et al. | 252/186.24 |
| 4,692,374 A | 9/1987 | Bouchette | 428/288 |
| 4,725,271 A | 2/1988 | Korol | 604/368 |
| 4,728,498 A * | 3/1988 | Theeuwes | 422/29 |
| 4,735,739 A | 4/1988 | Floyd et al. | 252/91 |
| 4,736,467 A | 4/1988 | Schwarze et al. | 2/114 |
| 4,737,405 A | 4/1988 | Bouchette | 428/288 |
| 4,740,398 A | 4/1988 | Bouchette | 428/28 |
| 4,772,492 A | 9/1988 | Bouchette | 427/342 |
| 4,781,974 A | 11/1988 | Bouchette et al. | 428/288 |
| 4,810,567 A | 3/1989 | Calcaterra et al. | 428/224 |
| 4,833,003 A | 5/1989 | Win et al. | 428/198 |
| 4,835,019 A | 5/1989 | White et al. | 427/387 |
| 4,837,079 A | 6/1989 | Quantrille et al. | 428/288 |
| 4,847,089 A | 7/1989 | Kramer et al. | 424/405 |
| 4,882,167 A | 11/1989 | Jang | 424/468 |
| 4,883,828 A | 11/1989 | Oakes et al. | 523/122 |
| 4,906,464 A | 3/1990 | Yamamoto et al. | 424/78 |
| 4,908,209 A | 3/1990 | McIntosh, Jr. et al. | 424/409 |
| 4,908,381 A | 3/1990 | Greenwald et al. | 514/460 |
| 4,917,686 A | 4/1990 | Bayston et al. | 604/265 |
| 4,929,498 A | 5/1990 | Suskind et al. | 428/288 |
| 4,938,955 A | 7/1990 | Niira et al. | 424/79 |
| 4,938,958 A | 7/1990 | Niira et al. | 424/79 |
| 4,990,144 A | 2/1991 | Blott | 604/304 |
| 4,997,425 A | 3/1991 | Shioya et al. | 604/304 |
| 4,999,386 A | 3/1991 | Oakes et al. | 523/122 |
| 5,006,339 A | 4/1991 | Bargery et al. | 424/404 |
| 5,011,602 A | 4/1991 | Totani et al. | 210/484 |
| 5,019,096 A | 5/1991 | Fox, Jr. et al. | 623/1 |
| 5,023,089 A | 6/1991 | Sakamoto et al. | 424/502 |
| 5,027,438 A | 7/1991 | Schwarze et al. | 2/114 |
| 5,037,843 A | 8/1991 | Schoenberg | 514/389 |
| 5,061,485 A | 10/1991 | Oakes et al. | 424/81 |
| 5,069,907 A | 12/1991 | Mixon et al. | 424/445 |
| 5,071,648 A | 12/1991 | Rosenblatt | 424/78.06 |
| 5,087,450 A | 2/1992 | Lister | 424/402 |
| 5,108,740 A | 4/1992 | Greenwald et al. | 424/78.32 |
| 5,120,813 A | 6/1992 | Ward, Jr. | 528/28 |
| 5,126,070 A | 6/1992 | Leifheit et al. | 252/186.36 |
| 5,133,090 A | 7/1992 | Modak et al. | 2/168 |
| 5,149,469 A | 9/1992 | Komatsuzaki et al. | 264/28 |
| 5,154,920 A | 10/1992 | Flesher et al. | 514/643 |
| 5,158,778 A | 10/1992 | Donovan et al. | 424/488 |
| 5,173,535 A | 12/1992 | Abrutyn | 525/54.3 |
| 5,178,870 A | 1/1993 | Schaeken et al. | 424/405 |
| 5,211,959 A | 5/1993 | Yoshii et al. | 424/489 |
| 5,213,884 A | 5/1993 | Fellows | 428/240 |
| 5,226,434 A | 7/1993 | Britton et al. | 132/321 |
| 5,227,168 A | 7/1993 | Chvapil et al. | 421/445 |
| 5,236,703 A | 8/1993 | Usala | 424/78.36 |
| 5,238,843 A | 8/1993 | Carpenter et al. | 435/264 |
| 5,242,985 A | 9/1993 | Shih et al. | 525/326.9 |
| 5,266,329 A | 11/1993 | Riley, Jr. | 424/430 |
| 5,284,703 A | 2/1994 | Everhart et al. | 428/283 |
| 5,293,648 A | 3/1994 | Finley | 2/243.1 |
| 5,298,252 A | 3/1994 | Hagiwara et al. | 424/409 |
| 5,317,987 A | 6/1994 | Muller et al. | 116/206 |
| 5,320,806 A | 6/1994 | Dziabo et al. | 422/29 |
| 5,322,695 A | 6/1994 | Shah et al. | 424/448 |
| 5,324,520 A | 6/1994 | Dunn et al. | 424/435 |
| 5,330,746 A | 7/1994 | Friedman et al. | 424/49 |
| 5,336,505 A | 8/1994 | Ng et al. | 424/486 |
| 5,340,581 A | 8/1994 | Tseng et al. | 424/401 |
| 5,344,411 A | 9/1994 | Domb et al. | 604/265 |
| 5,350,624 A | 9/1994 | Georger et al. | 428/219 |
| 5,356,803 A | 10/1994 | Carpenter et al. | 435/200 |
| 5,366,732 A | 11/1994 | Zighelboim R | 424/411 |
| 5,368,852 A | 11/1994 | Umemoto et al. | 424/78.1 |
| 5,378,475 A | 1/1995 | Smith et al. | 424/473 |
| 5,389,202 A | 2/1995 | Everhart et al. | 162/103 |
| 5,407,685 A | 4/1995 | Malchesky et al. | 424/449 |
| 5,408,022 A | 4/1995 | Imazato et al. | 526/259 |
| 5,413,788 A | 5/1995 | Edwards et al. | 424/409 |
| 5,421,898 A * | 6/1995 | Cavanagh | 134/7 |
| 5,429,854 A | 7/1995 | Currie et al. | 428/138 |
| 5,432,000 A | 7/1995 | Young, Sr. et al. | 428/372 |
| 5,447,684 A * | 9/1995 | Williams | 422/20 |
| 5,486,381 A | 1/1996 | Cleveland et al. | 427/294 |
| 5,487,896 A | 1/1996 | Modak et al. | 424/402 |
| 5,503,840 A | 4/1996 | Jacobson et al. | 424/421 |
| 5,536,768 A | 7/1996 | Kantner et al. | 524/376 |
| 5,554,373 A | 9/1996 | Seabrook et al. | 424/400 |
| 5,556,699 A | 9/1996 | Niira et al. | 428/323 |
| 5,565,361 A | 10/1996 | Mutsakis et al. | 435/299.1 |
| 5,573,841 A | 11/1996 | Adam et al. | 428/219 |
| 5,578,124 A | 11/1996 | Cleveland et al. | 118/50 |
| 5,578,315 A | 11/1996 | Chien et al. | 424/435 |
| 5,584,877 A | 12/1996 | Miyake et al. | 623/1 |
| 5,603,921 A | 2/1997 | Bowen | 424/49 |
| 5,611,938 A * | 3/1997 | Smolik et al. | 210/755 |
| 5,612,052 A | 3/1997 | Shalaby | 424/426 |
| 5,614,223 A | 3/1997 | Sipos | 424/489 |
| 5,616,315 A | 4/1997 | Masterman et al. | 424/54 |
| 5,629,081 A | 5/1997 | Richards et al. | 442/96 |
| 5,648,003 A | 7/1997 | Liang et al. | 219/211 |
| 5,652,049 A * | 7/1997 | Suzuki | 442/387 |
| 5,652,274 A | 7/1997 | Martin | 514/724 |
| 5,656,361 A | 8/1997 | Vogt et al. | 428/198 |
| 5,681,575 A | 10/1997 | Burrell et al. | 424/423 |
| 5,686,065 A | 11/1997 | Haney | 424/59 |
| 5,695,857 A | 12/1997 | Burrell et al. | 428/209 |
| 5,699,326 A | 12/1997 | Haas et al. | 368/327 |
| 5,702,992 A | 12/1997 | Martin et al. | 442/123 |
| 5,707,736 A | 1/1998 | Levy et al. | 428/375 |
| 5,723,132 A | 3/1998 | Tseng et al. | 424/401 |
| 5,730,994 A | 3/1998 | Askill et al. | 424/402 |
| 5,733,503 A | 3/1998 | Kowatsch et al. | 422/28 |
| 5,736,473 A * | 4/1998 | Cohen et al. | 442/239 |
| 5,744,150 A | 4/1998 | Cercone | 424/404 |
| 5,747,078 A | 5/1998 | De Jong et al. | 426/9 |
| 5,753,251 A | 5/1998 | Burrell et al. | 424/426 |
| 5,763,412 A | 6/1998 | Khan et al. | 514/23 |
| 5,770,182 A | 6/1998 | Fischer | 424/49 |
| 5,770,255 A | 6/1998 | Burrell et al. | 427/2.1 |
| 5,807,563 A | 9/1998 | Askill et al. | 424/402 |
| 5,811,113 A | 9/1998 | Dorr et al. | 424/404 |
| 5,817,325 A | 10/1998 | Sawan et al. | 424/411 |
| 5,820,607 A | 10/1998 | Tcholakian et al. | 604/265 |
| 5,827,925 A | 10/1998 | Tremont et al. | 525/102 |
| 5,829,442 A | 11/1998 | Cox et al. | 128/849 |
| 5,834,051 A | 11/1998 | Woloxzko et al. | 427/2.24 |
| 5,837,274 A | 11/1998 | Shick et al. | 424/406 |
| 5,837,275 A | 11/1998 | Burrell et al. | 424/409 |
| 5,840,674 A | 11/1998 | Yatvin et al. | 514/2 |
| 5,849,311 A | 12/1998 | Sawan et al. | 424/406 |
| 5,851,551 A | 12/1998 | Tseng et al. | 424/486 |

| | | | | |
|---|---|---|---|---|
| 5,853,760 A | 12/1998 | Cremer | | 424/484 |
| 5,853,859 A | 12/1998 | Levy et al. | | 428/196 |
| 5,855,208 A | 1/1999 | Askill et al. | | 128/849 |
| 5,856,364 A | 1/1999 | Martin | | 514/724 |
| 5,874,098 A | 2/1999 | Stevens et al. | | 424/408 |
| 5,891,811 A | 4/1999 | Ashida et al. | | 442/71 |
| 6,013,275 A | * 1/2000 | Konagaya et al. | | 424/443 |
| 6,258,249 B1 | * 7/2001 | Simpson | | 205/687 |

FOREIGN PATENT DOCUMENTS

| | | | |
|---|---|---|---|
| EP | 0869216 A1 | 10/1998 | D06M/16/00 |
| EP | 0875146 A1 | 11/1998 | A01N/59/16 |
| EP | 0600004 B1 | 12/1998 | A46B/11/00 |
| EP | 0890336 A1 | 1/1999 | A47L/13/17 |
| EP | 0565301 B1 | 2/1999 | A61K/47/48 |
| FR | 2431570 | 2/1980 | D21H/5/22 |
| GB | 2211092 A | 6/1989 | A01N/25/34 |
| JP | 1-311008 | 12/1989 | A01N/61/00 |
| WO | WO 89/05093 | 6/1989 | A01N/25/34 |
| WO | WO 90/02166 | 3/1990 | C11D/17/04 |
| WO | WO 91/03938 | 4/1991 | A01N/25/24 |
| WO | WO 92/22221 | 12/1992 | A23L/3/3571 |
| WO | WO 94/26317 | 11/1994 | A61L/2/16 |
| WO | WO 95/13704 | 5/1995 | A01N/59/16 |
| WO | WO 96/11666 | 4/1996 | A61K/7/16 |
| WO | WO 96/40361 | 12/1996 | A61M/39/16 |
| WO | WO 98/24890 | 6/1998 | C12N/9/02 |
| WO | WO 98/44962 | 10/1998 | A61L/25/00 |

OTHER PUBLICATIONS

Dialog Abstract 00423532/7 © 1998 of Japanese Patent JP 8205762A published Aug. 13, 1996 entitled Antimicrobial functional sheet for preserving animal protein.

Dialog Abstract 008079373/7 © 1998 of Japanese Patent JP 1257124A published Oct. 13, 1989 entitled Antibiotic aluminosilicate—obtd. by ion exchange of ions in aluminosilicate to alkaline earth or manganese ions.

Dialog Abstract 011141997 ® 1999 of CN 1080833A published Jan. 19, 1994 entitled Wet toilet paper and preparing method thereof.

Dialog Abstract 008146353 © 1999 of Japanese Patent JP 1311008A published Dec. 15, 1989 entitled Antibiotic and antifungal compsn.—comprises zeolite contg. antibiotic metal ion and resin e.g. acryl for processing.

Dialog Abstract 01824797/7 © 1998 of U.S. Pat. No. 4,882,167 published Nov. 21, 1989 entitled Dry direct compression compositions for controlled release dosage forms [matrix of hydrophobic carbohydrate polymer, digestive difficulty soluble wax, fatty acid or neutral lipid.].

Dialog Abstract 004062594 © 1999 of DE 3305265A published Aug. 16, 1984 entitled Hygenic toilet seat cover for one–time use—comprises piece of crepe toilet paper cut to shape of seat and provided with self–adhesive strips for attachment to seat.

WPI Acc No. 97–200913/199718 Abstract of U.S. Pat. No. 5,118,509A entitled inducing skin tolerance to sensitising drug—by continuously and co–entensively administering drug with corticosteroid, preferably hydrocortisone, to selected site.

Dialog Abstract 002274528 © 1999 of DE 2813421A published Oct. 4, 1979 entitled Perforated multiple crepe paper and tissue mat assembly—sprayed with antimycotic disinfectant and supported on abrasion–resistant backing.

Dialog Abstract 05750225/9 © 1999 entitled New Antimicrobial Agent to be Included in stainless steel products.

Dialog Abstract 00365165/7 © 1998 of Japanese Patent JP 7123963A published May 16, 1995 entitled Antimicrobial water absorbing sheet.

Dialog Abstract 00162494/7 © 1998 of West German Patent EP 206285 published Jun. 27, 1985 entitled Filter Cartridge for upgrading drinking water quality.

Dialog Abstract 008153158/7 © 1998 of Japanese Patent JP 1316303A published Dec. 21, 1989 entitled Hydrous antimicrobial agent—comprises inorganic carrier contg. antimicrobial agent and nonwoven fabric of e.g. polyester resin layer.

Abstract 009382194 of U.S. Pat. No. 5,186,927A published Feb. 16, 1993 entitled Antimicrobial compsn. for oral hygiene—comprises particles having an outer surface onto which antimicrobial agent has been adsorbed.

Derwent Abstract 010600920 © 1999 of Patent AU 9514811A published Jan. 25, 1996 entitled Antimicrobial laminate for bags for foodstuffs for gradual release—comprises substrate impervious to steam and pervious firm superposed through adhesive layer contg. polyallyl isothiocyanate cyclodextrin cpd.

Abstract 009382274 of U.S. Pat. No. 5,187,158A published Feb. 16, 1993 entitled New O–dihydropyridylcarbonyl prodrug derivs. of ribovarin–used for site specific and sustained delivery of antiviral agent to the brain, and is retained in the brain after oxidn. to quat. pyridinium form.

Abstract 009230315 of CA Patent 1307738C published Sep. 22, 1992 entitled Liposome(s) having out bilayer with asymmetric distribution—comprise ionisable lipid or ionisable protein, useful as a drug delivery systems.

Abstract 008636625 of CA Patent 2020966A published Jan. 13, 1991 entitled Biocompatible film–forming topical delivery system—comprises active salt of carboxylic acid–functional polymer with therapeutic agent.

Dialog Abstract 010620478 © 1999 of CA 2134498A published Nov. 26, 1995 entitled Cove base for building wall—has elongate flat plate containing antimicrobial agent released over time.

Abstract 003667575 of DE 3134152A published Mar. 17, 1983 entitled Antimicrobial carrier esp. for delivery to bone—is metal or plastics coil opt. with polymer coating.

Abstract 004653629 of EP 184629 A published Jun. 18, 1986 entitled Microbicidal tub for urine drainage bag—passively releases antimicrobial on emptying to prevent infection.

Dialog Abstract 009588282 © 1999 of EP 558913 A1 published Sep. 9, 1993 entitled Two component minocycline controlled release delivery system—comprises initial loading of rapid release granules and sec. loading of bleded polymer coated spherical granules.

Dialog Abstract 011058050 © 1999 of EP 748634 A2 published Dec. 18, 1996 entitled Surgical implant, esp. for use as vascular prosthesis—produced from or comprising resorbable material contg. antimicrobial agent, esp. gentamycin crobefate.

Abstract 004440566 ® 1999 of JP 60181029 A published Sep. 14, 1985 entitled Sustained release drug. prepn.—involves mixing a e.g. peptide, protein, antimicrobial or antitumor drug with lactic acide (co) polymer.

Abstract 008370474 © 1999 of JP 2180694 A published Jul. 13, 1990 entitled Contimination preventing system for sterile water producing system—includes container contg. gradual release alkali cpd. and having discharge opening dia. preventing contamination.

Abstract 009176092 © 1999 of JP 4208205A published Jul. 29, 1992 entitled Sustained release antimicrobial ally isothiocyanate compsn.—prepd. by dissolving allyl isothiocyanate in glycerine ester or high alcohol ester.

Abstract 010615628 © 1999 of JP 8012511A published Jan. 16, 1996 entitled Prodn. of sustained–release antimicrobial agent used to maintain freshness of e.g. processed food—comprises dissolving volatile antimicrobial component in organic solvent, adding starch and removing solvent.

Abstract 010853168 of JP 8165210 A published Jun. 25, 1996 entitled Prodn. of antimicrobial agents—involves radically polymerising poly(meth)acryllic acid ester cpds. in organic solvent contg. aq. soln. of silver, copper or zinc ions.

Abstract of 010853169 of JP 8165211A published Jun. 25, 1996 entitled Prodn. of antimicrobial agents—copolymerising polyacryllic or polymethacryclic acid ester cpds. and silver, copper or zinc (meth) acrylic acid salts, inorganic solvent.

Dialog Abstract 011029508 of JP 8277204A published Oct. 22, 1996 entitled Sustained release microorganism control prepn—prepd by coating liq drop contg microorganism control agent with hydrophobic until microparticle silicon oxide power.

Abstract 011665622 of JP 9315927A published Dec. 9, 1997 entitled Antimicrobial cosmetic—comprises water containing components released from copper or copper alloy at effective doses which give antimicrobial activity.

Abstract 011393337 of Rusian Patent RU 2071323C1 published Jan. 10, 1997 entitled Antiviral sustained release preparation for treating acute respiratory diseases and herpes—contg. salt based on adamantyl–methylamine cpd. and copolymer derived from vinyl alcohol and N–vinylamido–succinic acid.

Abstract 007135943 of WO 8702576A published May 7, 1987 entitled Vaginal delivery systems—consist of viscous emulsion with (non)lipoidal phases, which adheres to vaginal wall.

Abstract 007673497 of WO 8807853A published Oct. 20, 1988 entitled Liposomal Vesicles for sustained intraperitoneal delivery—comprise therapeutic agent encapsulated in phosphatidyl choline–contg. lipid vesicle.

Abstract 009122425 of WO 9211042 A1 published Jul. 9, 1992, entitled Compsns, for disinfecting contact lenses–comprising aq. hydrogen peroxide, and a hydrogen peroxide–reducing agent to enhance antimicrobial activity, from peroxidase.

Abstract 009342695 of WO 93100115 A1 published Jan. 7, 1993 entitled Adhesive patch for controlled release of vapours to surroundings—useful for therapeutic agents, insecticides, insect repellants, perfumes, etc.

Abstract 009382714 of WO 9302717 A1 published Feb. 18, 1993 entitled Adhesive prod. used as surgical or medical dressing—comprises emulsion adhesive contg. medicament, coated on support, giving good antimicrobial activity.

Dialog Abstract 009440678 of WO 9306921 A1 published Apr. 15, 1993 entitled Particles with internal lyotropic liq. crystalline and lamellar surface phases–form stable dispersions useful for e.g. sustained drug delivery, antigen presentation, nucleic acid transport etc.

Dialog Abstract 010298861 of WO 9513704 A1 published May 26, 1995 entitled Material for sustained release of antimicrobial metal, esp. silver—has atomic disorder so that ions etc., are released into electrolytes at increased rate, useful e.g. for coating medical devices.

Dialog Abstract 010426917of WO 9524430 A2 published Sep. 14, 1995 entitled New block and graft copolymers—comprising pH–sensitive and temp. sensitive polymer components, useful for drug delivery for sustained and controlled release.

Abstract Document No. 5595750 published Jan. 21, 1997 entitled Antimicrobial particles of silver and barium sulfate or zinc oxide.

Abstract Document No. 5869073 published Feb. 9, 1999 entitled Antimicrobial liquid compositions and methods for using them.

Dialog Abstract 010936562 ® 1999 of WO 9628141A1 published Sep. 19, 1996 entitled Muco–adhesive granules contg carbomer and inert filler—for sustained release of pharmaceutical in gastro–intestinal tract.

Dialog Abstract 011905997 ® of WO 9824007A published Jun. 4, 1998 entitled Single line automated fluid delivering method for dental unit water line treatment—involves locking out operating control of consumable water or aqueous solution delivery device to prevent operation of device during antimicrobial flushing.

Dialog Abstract 008128186 ® 1999 of ZA 8809601A published Oct. 25, 1989 entitled Implants contg. antimicrobial agent for slow release in animals.

Dialog Abstract 02495825/9 ® 1999 entitled AK Steel signs pact for healthier coating.

Publication by Wipex entitled Disinfectant Wipes with Indicator Stripes.

Article published in Letters in Applied Microbiology 1993, vol. 16 pp. 173–177 entitled An in–use study of the relationship between bacterial contamination of food preparation surfaces and cleaning cloths.

Article published in Journal of Applied Bacteriology 1990, Vol 68, pp. 271–278 entitled The survival and transfer of microbial contamination via cloths, hands and utensils.

Article published in J Antibact. Antifungi Agents, vol. 22, No. 9, pp. 531–536, 1994. entitled Antimicrobial Activities of Silver and Copper Ions.

Article published in Springer–Verlag Berlin Heidelberg New York 1980 by Erich Lueck entitled Antimicrobial Food Additives—Characteristics—Uses—Effects.

* cited by examiner

CONTROLLED RELEASE ANTI-MICROBIAL HARD SURFACE WIPER

This application claims the benefit of U.S. Provisional Application No. 60/173,224 filed Dec. 28, 1999.

FIELD OF THE INVENTION

The present invention generally relates to a wiper, such as the type used to disinfect hard surfaces in food service and medical applications. More particularly, the present invention is directed to a wiper having an anti-microbial agent that can be controllably released over an extended period of time and which remains effective after repeated washings and rinsings.

BACKGROUND OF THE INVENTION

Microbial contamination can have a detrimental effect on any item ordinarily used by consumers or merchants, particularly items used in the medical and food service industries. For example, due to various bacterial outbreaks, there have been at least 200 food poisoning deaths reported in the last 10 years. Moreover, more Americans die from hospital infections each year than from car accidents and homicides combined.

Much of this contamination occurs due to migration of microorganisms from hard surfaces such as table tops or counter tops to food or to the hands of food handlers and, thence, to the food itself. For example, in the food service industry, contamination commonly occurs on stainless steel surfaces used for food preparation. Various food products are prepared on hard surfaces such as counters, tables, and the like. Bacteria from these products will often collect on such surfaces and, if the surface is not disinfected regularly, will transfer from product to product or from a product to the food handler. Numerous studies indicate that cross-contamination occurs as a result of a microorganism coming into contact with a person's hands or a cleaning cloth and thereafter contaminating other items touched by the cloth or hands, such as equipment or other surfaces.

As a result, wipers that contain anti-microbial agents have been employed to prevent such surface and cloth contamination. Currently, most of these anti-microbial wipers are impregnated with anti-microbial agents and are delivered to the user in a premoistened form. With these pre-moistened wipers, however, the disinfecting agent within the wiper is commonly readily exhausted after washing and rinsing of the wiper to remove dirt after a period of use. Thus, it is believed that such premoistened wipers either inhibit growth on the wipers and/or the hard surfaces cleaned only mildly or may only be used for a limited number of wipes.

Some anti-microbial wipers have been developed that are not pre-moistened. For example, one such anti-microbial wiper that can be delivered in a dry condition is disclosed in U.S. Pat. No. 5,213,884 to Fellows. In the Fellows patent, a wiper is described that contains a hot melt adhesive powder mixed with a chlorine release agent. The adhesive powder and chlorine release agents are incorporated into a tissue suitable for use in the disinfection of hard surfaces.

Although the wiper disclosed by Fellows can be delivered in a dry form, it apparently fails to provide sufficient disinfection over an extended period of time—similar to pre-moistened wipers. After being contacted with water, the release of the anti-microbial agent in such wipers capable of being delivered in a dry state occurs readily without control. This prevents the wiper from sustaining its anti-microbial activity after repeated washings and rinsings.

Another anti-microbial wiper has been marketed by Pal International Inc. of England under the name WIPEX. According to sales literature, this wiper contains poly (hexamethylenebiguanide hydrochloride), alkyldimethybenzyl ammonium chloride, and the disodium salt of ethylenediaminetetraacetic acid (E.D.T.A.). In addition, the wipes include indicator stripes that are stated to fade gradually as the disinfectants in the wiper are depleted. It is believed that U.S. Pat. No. 4,311,479 to Fenn et al. is related to this particular anti-microbial cloth. It is unclear, however, whether these wipes would prove to be very effective in reducing cellular activity. Also, it is believed that they would retain only limited anti-microbial activity after washing and rinsing.

Accordingly, a need currently exists for a more effective wiper that disinfects hard surfaces and inhibits cross-contamination. In particular, a need exists for a wiper that contains an anti-microbial agent that is slowly released when contacted by water, thereby allowing the wiper to provide an anti-microbial solution and to sustain its anti-microbial effectiveness after repeated washing and rinsing operations.

SUMMARY OF THE INVENTION

Accordingly, an object of the present invention is to provide a wiper suitable for use in disinfecting hard surfaces.

It is another object of the present invention to provide a wiper containing an anti-microbial agent that can remain effective after repeated washing and rinsing operations.

Still another object of the present invention is to provide a wiper containing an anti-microbial agent that can remain effective after repeated washing and rinsing by controlling the release rate of the anti-microbial agent.

Yet another object of the present invention is to provide a wiper containing a controlled release anti-microbial agent that is incorporated within a fibrous substrate layer.

It is another object of the present invention to provide a wiper containing a controlled release anti-microbial agent incorporated within a hydrophobic substrate layer that adheres to a fibrous substrate material.

These and other objects of the present invention are achieved by providing a wiper suitable for disinfecting hard surfaces and inhibiting or preventing cross-contamination. A wiper of the present invention generally includes a substrate layer, at least one laminate layer, and an anti-microbial agent which is adhered to the substrate layer.

In accordance with the present invention, any material commonly used in the art to manufacture cleaning cloths, such as wipers, can be used as the substrate material. Commonly, but not restricted to such materials are hydrophobic materials. Generally, the substrate material may have a basis weight of more than about 10 grams per square meter (gsm). In one embodiment of the present invention, the wiper contains a meltblown substrate layer formed from poly(ethylene vinyl acetate) co-polymer (EVA).

In addition to a substrate layer, a wiper of the present invention also contains a laminate layer. In general, a laminate layer of the present invention can include any absorbent material (or if an additional laminate layer is employed, a hydrophobic material) that may be bonded to the substrate layer. For example, in one embodiment, two laminate layers formed from a hydroentangled material sold under the name HYDROKNIT® and having a basis weight of 49 gsm, are bonded to both surfaces of an EVA meltblown substrate layer. HYDROKNIT® is further disclosed in U.S. Pat. No. 5,284,703 to Everhart et al. which is incorporated herein in its entirety by reference thereto. In addition, the web can be a co-form material such as disclosed in U.S. Pat. No. 4,100,324 to Anderson et al. and U.S. Pat. No. 5,350,624 to Georger et al., which are incorporated herein in their entireties by reference thereto.

As stated, the substrate layer of the present invention can be hydrophobic. Consequently, such layers can have a substantial effect on water penetration because the layer itself has a thickness. As such, the substrate layer can enhance the ability of a wiper made according to the present invention to operate over an extended period of time after repeated washings and rinsings. In particular, when the substrate layer is hydrophobic, it is believed that the layer can inhibit water from readily migrating out of the wiper, thus providing a longer release time for an anti-microbial agent incorporated therein.

According to the present invention, a subject wiper also includes an anti-microbial agent that can be controllably released over an extended period of time after repeated washing and rinsing. "Repeated washing and rinsing", for purposes of the present invention, generally refers to at least 5 cycles of rinsing the wiper between wiping applications. As used herein a "rinse cycle" includes the steps of contacting the wiper with water and wringing or squeezing the excess water from the wiper. The anti-microbial agent is generally adhered to the fibers forming the substrate layer. In one particular embodiment, the anti-microbial agent is adhered to meltblown poly(ethylene vinyl acetate) (EVA) fibers.

In general, any anti-microbial agent capable of being controllably released can be used in accordance with the present invention. Some examples of anti-microbial agents that are suitable for use in the present invention include various solid particulate anti-microbial agents such as calcium hypochlorite particles, halogen generating formulations, chlorine dioxide generating formulations, particles containing silver ions, and quaternary amines complexed with a carrier.

In one embodiment of the present invention, an anti-microbial agent such as calcium hypochlorite, having different particle sizes is provided. Because smaller particles generally have higher rates of dissolution than larger particles, control of the release rate of the anti-microbial agent can be achieved through use of such particulates having a size differential.

Another embodiment of the present invention includes particulate forms of an anti-microbial agent that are coated with various polymers so that the particles are at least partially encapsulated. In this embodiment, various amounts and types of coatings may be provided to obtain the particular anti-microbial agent release rate desired. For example, a lower release rate is generally provided by a particle having a thicker or more complete coating, and vice-versa. In addition, mechanisms such as polymerization chemistries, porous absorbents, soluble binders, or combinations thereof, may be employed to modulate the controlled release properties of the anti-microbial agent.

The anti-microbial agent of the present invention may be incorporated into a substrate layer before the fibers comprising the substrate layer have become solidified. In one embodiment, calcium hypochlorite particles are added to unsolidified meltblown poly(ethylene vinyl acetate) fibers during formation of the meltblown substrate layer. The particles may be fed into the stream of meltblown fibers while the fibers are still tacky. If desired, the meltblown substrate layer containing calcium hypochlorite particles adhered to the EVA fibers may be formed directly onto a pre-formed absorbent laminate layer so that no additional adhesive is necessary to bond the laminate and substrate layers together, although the use of a separate adhesive for this purpose is within the scope of the present invention. The meltblown fibers are then allowed to solidify into a meltblown web. If desired, an additional laminate layer comprising the same material as the original laminate layer, or a different material, may be bonded to the other surface of the meltblown substrate layer. The additional laminate layer can be bonded to the substrate layer by any means, for example, by chemical or thermal bonding.

The substrate and the laminate layers of the present invention can also contain chemicals in addition to the anti-microbial agent. Moreover, a visual sensor or dye can be incorporated into one or more of the layers to indicate when the anti-microbial agent has been depleted. Some examples of such visual sensors are provided by the indicators described in U.S. Pat. Nos. 3,704,096; 4,205,043; 5,699,326; 5,317,987; 4,248,597 and 4,311,479, which are incorporated in their entireties by reference thereto. In addition, sodium thiosulfate and various blue dye mechanisms such as those employed herein in the WIPEX® wipes may also be employed.

Other objects, features and aspects of the present invention are discussed in greater detail below.

DETAILED DESCRIPTION OF REPRESENTATIVE EMBODIMENTS

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

In general, the present invention is directed to a wiper containing an anti-microbial agent that can be released to liquid contained within the wiper after a rinse cycle, where the agent is released at a controlled rate over a period of time. It has been discovered that by using an anti-microbial agent in solid or particulate form, the anti-microbial agent is slowly released when contacted by water. Surprisingly, this permits stronger anti-microbial agents to be employed than would be possible with wipers that do not control the release rate of the agent. Moreover, it has been found that the wiper can retain its anti-microbial activity over the course of multiple rinsing cycles. In fact, with certain embodiments of the present invention, as many as 6 or more rinsing cycles are possible. In other embodiments of the present invention, 10 or more rinsing cycles are possible, while in other embodiments of the present invention, 15 to 20 rinsing cycles can be obtained, and even 20 or more rinsing cycles are possible.

In accordance with the present invention, an anti-microbial surface wiper is provided that contains a substrate layer, at least one laminate layer, and an anti-microbial agent. In one embodiment, a wiper of the present invention includes a substrate layer that bonds with a first and second laminate layer. Further, an anti-microbial agent can be incorporated into the substrate layer such that the agent can be released at a controlled rate when contacted with water.

A laminate layer of the present invention can generally be made from any absorbent material commonly used in the art for wipers. For example, a laminate layer of the present invention can be made from absorbent nonwoven fabrics, and more particularly, from absorbent nonwoven composite fabrics having a high pulp concentration. Some examples of laminate layers that are suitable for use in the present invention are disclosed in U.S. Pat. No. 5,389,202 to Everhart et al., U.S. Pat. No. 5,284,703 to Everhart et al., and U.S. Pat. No. 5,573,841 to Adam et al., which are incorporated herein in their entireties by reference thereto. In one embodiment, the laminate layer(s) comprises a HYDROKNIT® nonwoven composite fabric that contains approximately 70% by weight pulp fibers that are hydraulically entangled into a continuous filament substrate. HYDROKNIT® material is commercially available from Kimberly-Clark Corporation of Neenah, Wis. In addition, the web can be a co-form material such as disclosed in U.S. Pat. Nos. 4,100,324 to Anderson et al. and U.S. Pat. No. 5,350,624 to Georger et al., which are incorporated herein in their entireties by reference thereto. The wipers may be packaged and made according to the disclosures of U.S. Pat. Nos. 4,833,003 and 4,853,281 to Win et al.

Depending on the particular application, the basis weight of a laminate layer used in accordance with the present invention can vary. In general, the basis weight of the laminate layer incorporated into a wiper of the present invention is at least about 10 grams per square meter (gsm). The basis weight of such laminate layer can also be at least about 20 gsm. In one embodiment of the present invention, the basis weight of the material used for the laminate layer is about 49 gsm.

Although not required, a wiper of the present invention may include more than one laminate layer. In one embodiment of the present invention, for example, the wiper includes two laminate layers, both of which can be made from an absorbent nonwoven fabric, such as a HYDROKNIT® material. In other embodiments, the additional laminate layer may itself be a hydrophobic material like one embodiment of the substrate layer. This allows the wiper to be engineered for specific performance criteria, such as for oil wiping.

A wiper made in accordance with the present invention includes a substrate layer that can adhere to the laminate layer, either through self-bonding or through the use of a separate adhesive bonding material. In particular, a substrate layer of the present invention is made from a fibrous material. In particular, a hydrophobic fibrous material can be used. Some examples of materials that are suitable for use in the substrate layer of the present invention are disclosed in U.S. Pat. No. 5,350,624 to Georger et al., which is incorporated in its entirety herein by reference thereto. Other examples of suitable substrate materials include, for example, meltblown polypropylene, spunbond polypropylene, HYDROKNIT® material, double recreped webs and tissue paper. In one particular embodiment of the present invention, the substrate layer comprises meltblown poly(ethylene vinyl acetate). One example of a commercially available form of poly(ethylene vinyl acetate) that is suitable for use in accordance with the present invention is EVA Grade LC 724.36, having a melt index of 135° C., made by EXXON Chemicals.

The substrate layers employed in the present invention may exhibit various basis weights. In one particular embodiment, when laminate layers of approximately 49 gsm are employed, the total composite may have a basis weight of between about 125 gsm and 130 gsm, and more particularly about 130 gsm.

When adhered to the laminate layer according to the present invention, the substrate layer is believed to contain void spaces that can increase the ability of the wiper to hold moisture. Each time the wiper is subjected to a rinse cycle, the liquid within the wiper, including the liquid within the substrate layer, is totally or partially exchanged with liquid from an external source (e.g., a wash bucket). Liquid that enters the wiper generally has very little or no content of anti-microbial agent dissolved therein, and consequently is a poor anti-microbial solution. However, the liquid that is in contact with the subject substrate layer—and the anti-microbial agent in controlled release form that is adhered thereto—dissolves a portion of the anti-microbial agent and thereby forms an anti-microbial solution.

As used herein, the terms "anti-microbial solution" mean a liquid having in solution an amount of an anti-microbial agent that is sufficient to kill or reduce the growth rate of strains of common disease causing bacteria as compared with the same liquid without that amount of anti-microbial agent. In some of the embodiments of this invention, it is possible for the anti-microbial solution to act as a sanitizer solution or a disinfectant solution.

When the wiper is used to cleanse surfaces, some of the retained wiper liquid is forced out of the wiper and is left on the surface. Since this liquid is an anti-microbial solution, it is capable of acting as a biocide or biostat on the surface that has been wiped.

It is believed that because the substrate layer has a measurable and controllable void volume, the amount of liquid that is retained within the layer after a rinse can be determined and controlled. Accordingly, the anti-microbial agent that is adhered to the substrate layer must only provide enough anti-microbial agent to make this retained liquid an anti-microbial solution. Therefore, by controlling the amount and form of anti-microbial agent that is adhered to the substrate layer, and by providing the substrate layer as a fibrous mat having a measurable and controllable void volume, one is able to control the amount of anti-microbial agent that enters the retained liquid after each rinse cycle, and thereby to provide a wiper that is capable of replenishing the anti-microbial agent in the retained liquid after numerous rinse cycles.

It is believed that the use of a hydrophobic fibrous web as the substrate layer can also affect the fluid retention properties of that layer, and can thereby provide desirable control over the controlled-release characteristics of the wiper.

Furthermore, in one embodiment, the substrate layer is contained between two separate absorbent laminate layers, which allows the wiper to retain good wipe-dry properties, while also possessing the ability to hold moisture and prevent or reduce the loss of particles of a non-activated, highly concentrated, anti-microbial agent. An advantage of this structure is that it permits the isolation of anti-microbial agents from direct touch with any surface that the wiper contacts. This is an advantage when using anti-microbial agents that are irritating to the skin, because it prevents particles or concentrated sources of such agents from being left on surfaces which may come in contact with human skin (e.g., toilet seats). In addition, it is believed that such wipers tend to be less irritating to the hands of the user.

As stated above, a wiper of the present invention also includes an anti-microbial agent that can be controllably released. Generally, the anti-microbial agent is incorporated into the substrate layer of the subject wiper. In particular, the anti-microbial agent may be added to the substrate layer while the substrate layer remains in an unsolidified state. By being added at this stage, the anti-microbial agent can be highly dispersed and become part of the substrate layer's fibrous web, thereby substantially prohibiting unwanted leakage of the agent. The cooling and solidification of the fibers into a structured web results in the adhesion of the particles to the substrate layer and substantially prevents them from being detached during repeating rinse cycles. The strength of adhesion of the particles to the substrate layer substantially prevents the migration of such particles from the substrate layer, and also reduces the loss of particles by abrasion.

In general, an anti-microbial agent of the present invention can comprise a number of different chemicals commonly used as disinfectants in the field. Useful anti-microbial agents include a chlorine dioxide-generating formulation containing chlorine dioxide, sodium chlorate surfactant, and an acid moiety as the anti-microbial agent. A commercially available example of such a controlled-release chlorine dioxide formulation is made by Bernard Technologies, Inc. and is sold under the name MICROSPHERE® 2500. This product may be described in U.S. Pat. Nos. 5,631,300; 5,639,295; 5,650,446; and 5,668,185.

In one embodiment of the present invention, the anti-microbial agent can include silver ions. In this embodiment, a silver-zeolite complex can be utilized to provide controlled release of the anti-microbial agent. One commercially available example of such a controlled-release anti-microbial agent has been available from AgION Technologies, LLC., under the name AgION™ (which was previously available under the name HEALTH SHIELD® from K. B. Technologies, Inc.). This material has been incorporated into a fabric, which is available under the name GUARDTEX®. This material is constructed from polyester and rayon and contains a silver-zeolite complex. Other suitable silver containing microbial agents are disclosed in Japanese Unexamined Patent No. JP 10/259325, which is incorporated herein by reference.

In addition to silver-zeolites, other metal-containing inorganic additives can also be used in the present invention. Examples of such additives include, but are not limited to, copper, zinc, mercury, antimony, lead, bismuth, cadmium, chromium, thallium, or other various additives, such as disclosed in Japanese Patent No. JP 1257124 A and U.S. Pat. No. 5,011,602 to Totani et al, which are incorporated herein by reference. In some embodiments, the activity of the additive can also be increased, such as described in U.S. Pat. No. 5,900,383 to Davis et al., which is also incorporated herein by reference.

In another embodiment of the present invention, the anti-microbial agent can be a material that is a source of free chlorine. Calcium hypochlorite or sodium hypochlorite can be used for this purpose, and calcium hypochlorite particles, in particular, can be useful. An example of a commercially available form of calcium hypochlorite particles suitable for use in the present invention is ALDRICH-brand #24-415-5 stabilized technical grade (ground and screened to approximately 150 micron particle size).

In addition to the above-mentioned embodiments, other anti-microbial agents can also be utilized in a wiper made in accordance with the present invention. Examples of such anti-microbial agents include, but are not limited to, quaternary amines, halogens, chlorine dioxide, oxidants, peroxides, such as sodium peroxide, other silver ions, such as $Ag^+$, $Ag^{++}$, and $Ag^{+++}$ and silver complexes, or combinations thereof. Some examples of systems that can be used to generate chlorine dioxide, for instance, are disclosed in U.S. Pat. Nos. 5,126,070; 5,407,685; 5,227,168; 4,689,169; and 4,681,739, all of which are incorporated herein in their entireties by reference thereto. Another anti-microbial agent which could be employed is disclosed in U.S. Pat. No. 5,837,274 to Shick et al. which is incorporated herein in its entirety by reference thereto.

The anti-microbial agent of the present invention can be in a form that provides control of the rate of release of the agent from its source into the liquid that is in contact with the agent. A variety of mechanisms for adjusting solubility are known in the art and can be employed to control the release rate of the anti-microbial agent incorporated within a wiper made according to the present invention.

In some embodiments of the present invention, anti-microbial particles having varying sizes can be employed to control the release of the agents. For example, the release rate of calcium hypochlorite can be controlled by employing hypochlorite particles that have a certain size distribution. Because they provide higher surface area, smaller calcium hypochlorite particles have a faster dissolution rate into water than larger particles. Thus, in one embodiment of the present invention, the rate of calcium hypochlorite release by the wiper can be controlled by providing particles of different sizes. To reduce the overall release rate, larger particle sizes can simply be added as needed to the controlled-release composition prior to incorporation into the substrate layer.

An example of such an anti-microbial controlled-release agent is disclosed in PCT Application No. WO 98/53679, entitled "Solid Disinfectant Material/Surfactant Compositions" and assigned to Olin Corporation. As described therein, disinfectant compositions are controllably released over time as anti-microbial agents.

In addition to varying particle size, other mechanisms for controlling release rate can be used to control the release of the anti-microbial agent present within a subject wiper. In particular, mechanisms for controlled release such as polymerization chemistries, encapsulation, porous absorbents, soluble binders, and other similar technologies can be employed to further enhance the ability to control the amount of anti-microbial agent released over a period of time.

For example, in one embodiment, calcium hypochlorite particles can be totally or partially encapsulated within a polymer coating to reduce the dissolution rate of the particles in water. By reducing the dissolution rate, the calcium hypochlorite is released in controlled amounts over a longer period of time, providing for the ability to withstand continued washing and rinsing, while still remaining effective as the anti-microbial agent of the wiper. When incorporating a coating with an anti-microbial agent of the present invention, any coating known in the art to reduce the release rate or dissolution rate of the agent can be used. For example, in one embodiment, an aqueous emulsion of an acrylic polymer is used to coat a calcium hypochlorite anti-microbial agent. In another embodiment, a microcrystalline wax coating can be used. In yet another embodiment, polyethylene can be used.

To sufficiently reduce the release rate of the anti-microbial agent in accordance with the present invention, it is not generally necessary to completely coat the particles. For instance, in one embodiment, a 20% acrylic polymer coating is used, while in another embodiment, a 33.5% acrylic polymer coating is used. In still another embodiment, a 60% microcrystalline wax coating is used.

According to the present invention, other chemicals can be incorporated into the subject wiper to enhance the performance of the wiper. For example, a wiper of the present invention can also contain surfactants, saponins, and other chemicals to control biofilm formation on the surface being cleaned. Furthermore, a wiper of the present invention can contain chemicals that act as visual sensors to detect the exhaustion of the anti-microbial agent. In particular, an indicator can be incorporated into a clear binder contained within the wiper to communicate an exhaustion of the anti-microbial agent by changing color. Several indicator methods are known in the art and may be utilized in the present invention. Examples include time indicators, chemical indicators, pH indicators, binder/dye indicators, and dye solubility indicators.

A method for producing an anti-microbial wiper of the present invention may be generally described as follows. It should be noted that the discussion below is intended only as a description sufficient to enable one skilled in the art to produce an embodiment of an anti-microbial wiper of the present invention. Other similar processes known in the art are also suitable for producing the anti-microbial wipers of the present invention.

To produce a wiper of the present invention, the anti-microbial agent is first generally entrapped within the substrate layer while the substrate layer remains in an unsolidified state. In particular, calcium hypochlorite particles, for example, may be entrapped within an unsolidified fibrous web of a poly(ethylene vinyl acetate) meltblown substrate layer. Other means could be employed, however, to attach the particles to the fibers. One example that could be utilized is disclosed in U.S. Pat. No. 5,736,473 to Cohen et al. which is incorporated herein in its entirety by reference thereto. Cohen et al. disclose a method of attaching a particulate material to individual surfaces of a fibrous material by employing an electrically charged matrix of fibrous material.

In one particular embodiment of the present invention, poly(ethylene vinyl acetate) (EXXON EVA Grade LC 724.36, melt index 135° C.) is initially meltblown into a fibrous web. Processes and apparatuses employed for producing meltblown fibers and the resulting nonwoven webs are well known in the art. Meltblown fibers are fibers formed by extruding a molten polymeric material through a plurality of fine, usually circular, die capillaries as molten threads or filaments into converging, usually hot and high velocity, gas (e.g. air) streams to attenuate the filaments of molten material and form fibers. During the meltblowing process, the diameters of the molten filaments are generally reduced by the force exerted by the drawing air to a desired size. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Buntin et al, U.S. Pat. No. 4,526,733 to Lau, and U.S. Pat. No. 5,160,746 to Dodge, II et al., all of which are hereby incorporated herein in their entireties by reference thereto. Meltblown fibers may be continuous or discontinuous and are generally smaller than ten microns in average diameter. Various materials may be used to form the meltblown fibers such as polyethylene or polypropylene.

In one embodiment, poly(ethylene vinyl acetate) is extruded at a temperature such as 420° F., at an extruder pressure of, for example, 135 psig, and at a primary attenuation air temperature of, for example, 435° F. After extrusion, calcium hypochlorite particles (ALDRICH #24-415-5 stabilized granular technical grade) are then delivered to the meltblown poly(ethylene vinyl acetate) stream using a hopper apparatus having a regulated metering roll and are metered at 16.8 g/min (~12.4 g/m$^2$) over a 7" width of the meltblown ethyl vinyl acetate stream.

The discharge nozzle of the hopper apparatus is generally in close proximity to the hot exiting meltblown poly (ethylene vinyl acetate) fibers to facilitate adherence of the calcium hypochlorite particles to the molten fibers and to form the fibers into a consolidated web. The nozzle of the hopper apparatus may be spaced about 3 inches to about 4 inches, or less, away from the exiting fibers such that a consolidated web with a basis weight of approximately 24 grams per square meter can be formed.

After forming the poly(ethylene vinyl acetate)/calcium hypochlorite composite substrate layer, it is then necessary to bond the composite to one or more laminate layers for forming the subject hard surface wiper. A standard 49 gram per square meter HYDROKNIT® material may be employed as the absorbent laminate layer by being unwound upstream of the composite stream and positioned onto a foraminous forming wire operating at about 25 feet per minute. The tacky composite may then be formed directly onto the HYDROKNIT® material without adhering to the wire itself.

Thereafter, if desired, a second laminate layer may be adhered to the composite substrate layer. A second 49-gsm HYDROKNIT® material is likewise thermally bonded to the composite such that the substrate layer is positioned between the first and second laminate layers to act as an adhesive between the layers. In this regard, the spunbond sides of each layer of HYDROKNIT® material typically face the composite substrate layer.

After the three layers are appropriately positioned, a thermal bonder may be utilized to bond together the layers using a bond pattern (such as a "714 bond pattern" as described in U.S. Pat. No. 5,389,202, which is incorporated herein in its entirety by reference thereto) roll positioned against a smooth steel roll. The roll parameters may be adjusted such that the roll temperature is, for example, about 214° F., the bonding pressure is, for example, about 30 psig, and the line speed is, for example, about 10 feet per minute. As a result of the above described process, the anti-microbial agents (in one embodiment, calcium hypochlorite particles) are sufficiently positioned between the laminate layers within the substrate matrix such that only a negligible amount of particles are lost during mechanical working of the web when either dry or wet.

The present invention may be better understood with reference to the following examples.

EXAMPLE 1

The general concept of controlled release as it relates to a wiper of the present invention was demonstrated as follows. Two 4"×6" samples of wipers were prepared. Both wipers contained two 49 gsm layers of HYDROKNIT® laminate material, bonded to a 24 gsm meltblown poly (ethylene vinyl acetate) (EXXON EVA Grade LC 724.36, melt index 135° C.) substrate material as described above. The substrate material that was used in one of the samples included ALDRICH-brand calcium hypochlorite particles (Aldrich #24-415-5 stabilized granular technical grade granulated to various particle sizes; all particles of which <105 mesh) that were adhered to the meltblown fibers in accordance with the present invention. The other sample contained no anti-microbial agent.

After preparation, the provision of chlorine as an anti-microbial agent was measured for the two wiper samples by using Hach's DPD (N, N-diethyl-p-phenylenediamine) test for measuring total chlorine content. Hach's DPD test is accepted by the United States Environmental Protection Agency for determining chlorine content and is a widely available test that employs a calorimeter and various DPD reagents.

To test the content of a sample using Hach's DPD method, at least 25 ml to 40 ml of a sample is collected in a beaker. The contents of a DPD Total Chlorine Powder Pillow or an AccuVac ampul are then added to the sample. The DPD pillow and ampul contain N, N-diethyl-p-phenylenediamine, i.e. DPD, and iodide. When added to a sample, combined chlorine in the sample oxidizes the iodide to form iodine. The iodine in turn reacts with the DPD along with any free chlorine available in the sample to form a red color that is proportional to the total chlorine concentration. The sample is allowed to react with the DPD pillow or ampul reactant for three minutes. After sufficient reaction time, the sample's total chlorine content was measured by measuring the light absorbance of the reacted sample at a specific wavelength. Hach's DPD Method for testing total chlorine concentration is adapted from *Standard Methods for the Examination of Water and Wastewater.*

To provide initial water activation, each wiper sample was placed in a standard one-liter laboratory beaker containing 500 ml of deionized water for 60 seconds. Once placed in water, each sample was agitated using mild stirring with a magnetic bar. After stirring, the samples were then removed from their respective beakers, hung vertically, and allowed to drip free. Subsequently, the samples were run through an Atlas Laboratory Wringer (unloaded without weight). After the samples were allowed to drip and were wrung out, approximately 1 ml to 1.5 ml of fluid was collected from each wiper sample and collected in a clean tray. The collected fluid from each wiper sample was diluted to 100 ml. The combination of contact with water, followed by free drip and then by wringing, is referred to generally herein as a rinse cycle. A normal rinse cycle under typical use conditions would be considered to be a manual rinse of the wiper with water, followed by a hand wringing.

Hach's DPD test was then performed on the samples at the time intervals listed in Tables 1 & 2 for each wiper sample. Table 1 represents the results with the wiper having no controlled-release anti-microbial agent; Table 2 represents the results with the wiper having the calcium hypochlorite anti-microbial agent.

TABLE 1

HYDROKNIT ®/EVA COMPOSITE WITHOUT TIMED RELEASE ANTI-MICROBIAL AGENT

| Sample (untreated) | Dry wt. (gm) | Wet wt. (gm before wringer) | Total Chlorine (ppm*) |
|---|---|---|---|
| 0 min. | 2.18 | — | — |
| 1 min. | — | — | <200* |
| 5 min. | — | — | <300* |

*Background test noise, Below the sensitivity of the diluted sample.

TABLE 2

HYDROKNIT ®/EVA COMPOSITE WITH TIMED RELEASE ANTI-MICROBIAL AGENT

| Sample (treated) | Dry wt. (gm) | Wet wt. (gm before wringer) | Total Chlorine (ppm*) |
|---|---|---|---|
| 0 min. | 2.02 | — | — |
| 1 min. | — | 8.6 | 9000 |
| 5 min. | — | 8.3 | 16700 |
| 10 min. | — | 7.9 | 14400 |
| 15 min. | — | 8.0 | 2600 |
| 20 min. | — | 8.3 | 800 |

From these examples, the controlled release of an anti-microbial agent over time with repeated wash and rinse stages was demonstrated. In particular, as shown in Table 2, the amount of total chlorine released over a 20-minute time period (and after 5 wash/rinse cycles) indicates that an anti-microbial agent can be released over an extended period of time, even after substantial washing and rinsing cycles.

It should be noted that the above tests were intended only as a method of demonstrating the controlled release potential of a wiper of the present invention. It should be understood that wipers of the present invention can demonstrate longer release times, e.g. 8 hours, and lower chlorine concentrations that comply with FDA regulations requiring no more than 200 ppm of chlorine in a sanitizing solution for food service applications.

For example, by treating calcium hypochlorite particles with coatings, such as acrylic acid or polyethylene, so as to at least partially encapsulate the particles, controlled dissolving rates can be achieved.

EXAMPLE 2

The ability of various anti-microbial agent coatings to provide controlled release rate was next demonstrated follows. Samples of ALDRICH-brand calcium hypochlorite particles (Aldrich #24-415-5 stabilized granular technical grade) were ground to a particle size between about 150 to 200 microns. The particles used in Sample #1, the control, were tested without the addition of a coating. Samples #2—#4 of the particles were coated with a 20% acrylic coating, a 33.5% acrylic coating, and a 60% microcrystalline polyethylene wax coating, respectively, prior to use.

After preparation, the rate of release of chlorine from all samples was measured by using the Hach's #8167 DPD (N, N-diethyl-p-phenylenediamine) test for measuring total chlorine content as discussed in Example 1.

To provide initial water activation, each sample was placed in a standard one-liter laboratory beaker containing deionized water and mildly stirred for 120 seconds with a magnetic bar. After stirring, undissolved particles were allowed to float or settle. The first sample, 10 ml in size, was then taken (called zero time or 0 min. in Table 3 below). Thereafter, 10 ml samples were taken at the time periods shown below. The samples were stored for 3 to 4 days in the dark and under refrigeration to significantly prevent chlorine degradation.

The testing procedure described above in Example 1, and as further described above, was repeated for each particle sample listed in Table 3. Table 3 shows the results for calcium hypochlorite particles having no coating, having a partial 20% acrylic coating, having a partial 33.5% acrylic coating, and having a 60% partial microcrystalline wax coating.

TABLE 3

CHLORINE RELEASE RATES FOR CALCIUM HYPOCHLORITE
PARTICLES HAVING VARIOUS COATINGS

AMOUNT OF CHLORINE RELEASED (mg/l)

| TIME OF WATER CONTACT (min.) | NO COATING | 20% ACRYLIC COATING | 33.5% ACRYLIC COATING | 60% POLYETHYLENE WAX COATING |
|---|---|---|---|---|
| 0 min. | 1.25 | 0 | 1.5 | 0 |
| 1 min. | 313 | 3 | 0.5 | 33 |
| 2 min. | 315 | 4 | 1.5 | 49.5 |
| 5 min. | 335 | 6 | 0.25 | 42 |
| 10 min. | 325 | 13 | 1 | 46 |
| 15 min. | 330 | 18 | 87.5[a] | 58 |
| 20 min. | 330 | 24 | 2 | 48 |
| 30 min. | 340 | 32 | 2.5 | 72 |
| 60 min. | 325 | 60 | 7 | 78 |
| 120 min. | 330 | 162 | 16 | 122 |
| 180 min. | 330 | 166 | 29 | 124 |
| 240 min. | 330 | 190 | 64 | 124 |
| 300 min. | n/a[b] | 180 | n/a | 122 |
| 1380 min. | n/a | 188 | n/a | 110 |
| 1440 min. | 340 | n/a | 84 | n/a |

Notes:
[a]Believed to be contaminated
[b]n/a means "not available" or "not measured".

From these examples, the controlled release of a coated anti-microbial agent over time was demonstrated. In particular, as shown in Table 3, anti-microbial agents at least partially coated with acrylic acid polymers and microcrystalline waxes exhibited much slower dissolving rates than did similar samples lacking such coating materials. It should be noted that the above tests were intended only as a method of demonstrating the controlled release potential of a wiper of the present invention.

EXAMPLE 3

The ability of an anti-microbial wiper of the present invention to disinfect a particular surface was also demonstrated. To quantify the wiper's kill efficacy, an indirect test was utilized. In general, adenosine tri-phosphate (ATP) can be measured and correlated with the number or mass of microorganisms on a particular surface. When ATP reacts with luciferin/luciferase, a reaction occurs that produces light, which can be measured photometrically to determine the corresponding amount of ATP present.

For this example, HY-LITE's ATP test method was used to determine the amount of ATP. The HY-LITE Hygiene Monitoring System (available as a kit from EM Science, which is a division of EM Industries, Inc.) employs the chemical reaction of luciferin/luciferase reagent with ATP to produce light, the intensity of which is measured by a calorimeter. The amount of light produced can then be correlated with the quantity of ATP present in the sample. The intensity of the light emitted from a sample placed in a HY-LITE Data Logger will be displayed in relative light units which relate directly to the quantity of ATP, and thus to the amount of biological matter left on a surface that is tested.

For these tests, two 4"×6" samples of wipers were prepared. Both wipers contained two layers of HYDROKNIT® laminate material, bonded to a meltblown poly(ethylene vinyl acetate) (EXXON EVA Grade LC 724.36, melt index 135° C.) substrate material as described above. ALDRICH-brand calcium hypochlorite particles (Aldrich #24-415-5 stabilized granular technical grade) were included as a component in one of the samples in accordance with the present invention. One sample did not contain an antimicrobial agent.

After preparation, the two wiper samples were placed in a standard one-liter laboratory beaker containing 1000 ml of potable water for 90 seconds. Thereafter, both wiper samples were removed from the beakers and hung until dripping ceased.

To test the kill efficacy of the wipers, a horizontally positioned sheet of 2'×2' restaurant grade stainless steel was provided. A 4"×4" grid on the stainless steel was marked and inoculated. A circle, approximately 6" in diameter, was outlined over the 4"×4" grid. Two suspensions of yeast cells were then prepared at different contamination levels. For higher levels of contamination, a 0.2% by weight suspension of dry baker's yeast (~40,000 yeast cells/60 μL assay) was used. For lower levels of contamination, a yeast cell suspension was prepared having approximately 1,000 yeast cells/60 μL assay.

Once prepared, each contamination level of yeast cells was separately tested by inoculating the particular suspension on the 4"×4" grid located on the stainless steel surface. For each contamination level, the treated and untreated 4"×6" wipers were tested. Using each respective wiper, the 6" diameter circle within the 4"×4" grid was cleaned using a circular motion (10 times with full 360° revolutions) at about the same hand pressure. The cleaned surfaces were allowed to sit 10 minutes before the concentration of residual microorganisms was determined by using HY-LITE's ATP Swab test. The experiment was again repeated for each wiper after cleaning the surface with bleach and thoroughly rinsing it with water.

For the higher level of yeast cell contamination, the untreated wiper had a 90% kill/removal level, while the treated wiper had a 99% kill/removal level. For the lower level of yeast cell contamination, the untreated wiper again had a 90% kill/removal level, while the treated wiper had a 99% kill/removal level.

From this example, the kill efficacy of a wiper of the present invention was demonstrated. Due to the time release mechanisms of the present invention, stronger anti-microbial agents can be utilized, thereby providing better kill efficacy than past anti-microbial wipers.

Although various embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. A wiper for disinfecting hard surfaces comprising:
   a fibrous laminate layer, said fibrous laminate layer being capable of absorbing a liquid when contacted therewith;
   a fibrous substrate layer having fibers therein with individually exposed surfaces thereon, said fibrous substrate layer being adhered to said fibrous laminate layer; and
   an anti-microbial agent distributed within the fibrous substrate layer and adhered to the individually exposed surfaces of the fibers in the fibrous substrate layer, said anti-microbial agent being capable of activation when contacted with a liquid, said activation including the release of a portion of said anti-microbial agent into said liquid that is contained within the wiper such that an anti-microbial solution forms therefrom, the anti-microbial agent being adapted to provide that the rate of said release is sufficient to ensure that an anti-microbial solution is formed in the liquid within the wiper after said wiper has been subjected to at least five rinsings; and said wiper being able to withstand at least 10 rinse cycles without substantially losing its ability to cause the liquid within the wiper after a rinse cycle to become an anti-microbial solution.

2. A wiper as defined in claim 1, wherein said anti-microbial agent comprises hypochlorite particles.

3. A wiper as defined in claim 2, wherein said hypochlorite particles are at least partially encapsulated to provide further control over said release into said liquid.

4. A wiper as defined in claim 2, wherein said hypochlorite particles are at least partially coated with a polymer to provide further control over said release into said liquid.

5. A wiper as defined in claim 2, wherein said hypochlorite particles comprise calcium hypochlorite.

6. A wiper as defined in claim 1, further including anti-microbial agents in the form of particles, wherein said particles have different particle sizes such that release of said anti-microbial agent is controlled by the presence of different sizes of anti-microbial agent particles.

7. A wiper as defined in claim 1, wherein the fibrous substrate layer comprises a hydrophobic material.

8. A wiper as defined in claim 1, wherein said fibrous substrate layer comprises a meltblown material selected from the group consisting of poly(ethylene vinyl acetate), polyester polypropylene and polyethylene.

9. A wiper as defined in claim 1, wherein said fibrous laminate layer comprises a nonwoven fabric.

10. A wiper as defined in claim 9, wherein said nonwoven fabric includes pulp fibers.

11. A wiper as defined in claim 1, wherein said anti-microbial agent comprises a chlorine dioxide-generating formulation.

12. A wiper as defined in claim 11, wherein said anti-microbial agent comprises sodium chlorate and an acid moiety.

13. A wiper as defined in claim 1, wherein said anti-microbial agent comprises a silver-containing additive.

14. A wiper as defined in claim 13, wherein said anti-microbial agent comprises silver zeolite.

15. A wiper as defined in claim 1, wherein said anti-microbial agent comprises quaternary amines.

16. A wiper as defined in claim 1, wherein said anti-microbial agent comprises a peroxide.

17. A wiper as defined in claim 1, wherein said anti-microbial agent is at least partially encapsulated to provide further control over the release of said anti-microbial agent.

18. A wiper as defined in claim 1, wherein said anti-microbial agent is at least partially polymer-encapsulated to provide further control over the release of said anti-microbial agent.

19. A wiper as defined in claim 1, wherein said wiper further comprises a surfactant.

20. A wiper as defined in claim 1, wherein said wiper further comprises a saponin.

21. A wiper as defined in claim 1, wherein said wiper further comprises a visual sensor to detect the exhaustion of said anti-microbial agent.

22. A wiper as defined in claim 1, comprising an additional fibrous laminate layer adhered to said fibrous substrate layer such that said fibrous substrate layer is positioned between two fibrous laminate layers.

23. A wiper as defined in claim 1, wherein said fibrous laminate layer has a basis weight of more than about 10 grams per square meter.

24. A wiper as defined in claim 1, wherein said substrate layer is self-adhered to said laminate layer.

25. A wiper as defined in claim 1 that will withstand at least 20 rinse cycles without substantially losing its ability to cause the liquid within the wiper after a rinse cycle to become an anti-microbial solution.

26. A wiper for disinfecting hard surfaces comprising:

a first fibrous laminate layer, said first fibrous laminate layer being capable of absorbing a liquid when contacted therewith, said first fibrous laminate layer being made from a nonwoven fabric having a basis weight of more than about 10 grams per square meter;

a second fibrous laminate layer, said second fibrous laminate layer being capable of absorbing a liquid when contacted therewith, said second fibrous laminate layer being made from a nonwoven fabric having a basis weight of more than about 10 grams per square meter;

a fibrous substrate layer having fibers therein with individually exposed surfaces thereon, said fibrous substrate layer being positioned between and adhered to said first fibrous laminate layer and said second fibrous laminate layer, said fibrous substrate layer being hydrophobic; and an anti-microbial agent distributed within the fibrous substrate layer and adhered to the individually exposed surfaces of the fibers in the fibrous substrate layer, and incorporated in a stabilized solid state within said fibrous substrate layer, said anti-microbial agent being capable of activation when contacted with water, said activation including the release of a portion of said anti-microbial agent into said liquid that is contained within the wiper such that an anti-microbial solution forms therefrom, the anti-microbial agent being adapted to provide that the rate of said release is such that said anti-microbial agent is released into said liquid in an amount sufficient to form an anti-microbial solution of the liquid within the wiper after said wiper has been repeatedly contacted with water; and said wiper being able to withstand at least 10 rinse cycles without substantially losing its ability to cause the liquid within the wiper after a rinse cycle to become an anti-microbial solution.

27. A wiper as defined in claim 26, wherein said fibrous substrate layer comprises meltblown poly(ethylene vinyl acetate).

28. A wiper as defined in claim 26, wherein said anti-microbial agent comprises calcium hypochlorite.

29. A wiper having at least two layers, one of said layers being a fibrous hydrophobic sheet comprising fibers having individually exposed surfaces thereon, said sheet having an anti-microbial agent distributed within the fibrous hydrophobic sheet and adhered to the individually exposed surfaces of the fibers in the sheet with sufficient adhesion so that said anti-microbial agent will remain substantially bonded within said sheet until contacted repeatedly with a liquid, the other of said layers being an absorbent fibrous sheet laminated to said fibrous hydrophobic sheet, and said wiper being able to withstand at least 10 rinse cycles without substantially losing its ability to cause the liquid within the wiper after a rinse cycle to become an anti-microbial solution.

30. A wiper as defined in claim 29, further comprising an additional sheet laminated to said fibrous hydrophobic sheet.

31. A wiper as defined in claim 30, wherein said additional sheet is absorbent.

32. A wiper as defined in claim 30, wherein said additional sheet is hydrophobic.

33. A wiper for disinfecting hard surfaces comprising:
    a fibrous laminate layer, said fibrous laminate layer being capable of absorbing a liquid when contacted therewith;
    a fibrous substrate layer having fibers therein with individually exposed surfaces thereon, said fibrous substrate layer being adhered to said fibrous laminate layer;
    an anti-microbial agent distributed within the fibrous substrate layer and adhered to the individually exposed surfaces of the fibers in the fibrous substrate layer, said anti-microbial agent being capable of activation when contacted with a liquid, said activation including the release of a portion of said anti-microbial agent into said liquid that is contained within the wiper such that an anti-microbial solution forms therefrom, the anti-microbial agent being adapted to provide that the rate of said release is sufficient to ensure that an anti-microbial solution is formed in the liquid within the wiper after said wiper has been subjected to at least five rinsing cycles; and
    a saponin.

34. A wiper for disinfecting hard surfaces comprising:
    a fibrous laminate layer, said fibrous laminate layer being capable of absorbing a liquid when contacted therewith;
    a fibrous substrate layer having fibers therein with individually exposed surfaces thereon, said fibrous substrate layer being adhered to said fibrous laminate layer; and
    an anti-microbial agent distributed within the fibrous substrate layer and adhered to the individually exposed surfaces of the fibers in the fibrous substrate layer, said anti-microbial agent being capable of activation when contacted with a liquid, said activation including the release of a portion of said anti-microbial agent into said liquid that is contained within the wiper such that an anti-microbial solution forms therefrom, the anti-microbial agent being adapted to provide that the rate of said release is sufficient to ensure that an anti-microbial solution is formed in the liquid within the wiper after said wiper has been subjected to at least five rinsing cycles, and said anti-microbial agent being at least partially encapsulated to provide further control over the release of said anti-microbial agent.

35. A wiper as defined in claim 34, wherein said anti-microbial agent is at least partially polymer-encapsulated to provide further control over the release of said anti-microbial agent.

36. A wiper as defined in claim 34, wherein said anti-microbial agent comprises hypochlorite particles.

37. A wiper as defined in claim 34, further including anti-microbial agents in the form of particles, wherein said particles have different particle sizes such that release of said anti-microbial agent is controlled by the presence of different sizes of anti-microbial agent particles.

38. A wiper as defined in claim 34, wherein the fibrous substrate layer comprises a hydrophobic material.

39. A wiper as defined in claim 34, wherein said fibrous substrate layer comprises a meltblown material selected from the group consisting of poly(ethylene vinyl acetate), polyester polypropylene and polyethylene.

40. A wiper as defined in claim 34, wherein said fibrous laminate layer comprises a nonwoven fabric.

41. A wiper as defined in claim 40, wherein said nonwoven fabric includes pulp fibers.

42. A wiper as defined in claim 34, wherein said anti-microbial agent comprises a chlorine dioxide-generating formulation.

43. A wiper as defined in claim 34, wherein said anti-microbial agent comprises a silver-containing additive.

44. A wiper as defined in claim 43, wherein said anti-microbial agent comprises silver zeolite.

45. A wiper as defined in claim 34, wherein said anti-microbial agent comprises quaternary amines.

46. A wiper as defined in claim 34, wherein said anti-microbial agent comprises a peroxide.

47. A wiper as defined in claim 34, wherein said wiper further comprises a saponin.

48. A wiper as defined in claim 34, wherein said wiper further comprises a visual sensor to detect the exhaustion of said anti-microbial agent.

49. A wiper as defined in claim 34, comprising an additional fibrous laminate layer adhered to said fibrous substrate layer such that said fibrous substrate layer is positioned between two fibrous laminate layers.

50. A method of forming an anti-microbial wiper for disinfecting hard surfaces, said method comprising the steps of:
    providing fibers that are capable of forming a web;
    adding an anti-microbial agent to said fibers while said fibers are in an unsolidified state;
    allowing said fibers to solidify into a fibrous web, wherein said anti-microbial agent is adhered to said fibrous web, said anti-microbial agent being capable of activation when contacted with water, said activation including the release of a portion of said anti-microbial agent into water contained in said fibrous web such that an anti-microbial solution forms therefrom after a normal rinse cycle, said anti-microbial agent being capable of forming said anti-microbial solution after numerous rinse cycles; and
    laminating said fibrous web containing said anti-microbial agent to a laminate layer, wherein said laminate layer is capable of absorbing a liquid when contacted therewith.

51. A method as defined in claim 50, wherein said fibers are hydrophobic.

52. A method as defined in claim 51, wherein said hydrophobic fibers comprise poly(ethylene vinyl acetate).

53. A method as defined in claim 51, wherein said fibrous web comprises meltblown hydrophobic fibers.

54. A method as defined in claim 50, wherein said laminate layer is made from a nonwoven composite fabric, said nonwoven composite fabric comprising pulp fibers.

* * * * *

UNITED STATES PATENT AND TRADEMARK OFFICE
CERTIFICATE OF CORRECTION

PATENT NO. : 6,734,157 B2
APPLICATION NO. : 09/746720
DATED : May 11, 2004
INVENTOR(S) : Fred Radwanski, James Clark and Ralph Anderson It is certified that error appears in the above-identified patent and that said Letters Patent is hereby corrected as shown below:

Item (56) References Cited

OTHER PUBLICATIONS
   (Pg. 3) Dialog Abstract 009588282, "sec. loading of bleded" should read -- sec. loading of blended --
   (Pg. 3) "Dialog Abstract 004440566 ® 1999" should read -- Dialog Abstract 004440566 © 1999 --
   (Pg. 4) "Dialog Abstract 010936562 ® 1999" should read -- Dialog Abstract 010936562 © 1999 --
   (Pg. 4) "Dialog Abstract 011905997 ® of" should read -- Dialog Abstract 011905997 © of --
   (Pg. 4) "Dialog Abstract 008128186 ® 1999" should read -- Dialog Abstract 008128186 © 1999 --
   (Pg. 4) "Dialog Abstract 02495825/9 ® 1999" should read -- Dialog Abstract 02495825/9 © 1999 --

Column 15, line 10 (Claim 1) "rinsing; and" should read -- rinsing cycles; and --

Signed and Sealed this

Thirtieth Day of January, 2007

JON W. DUDAS
*Director of the United States Patent and Trademark Office*